United States Patent [19]
Noelle et al.

[11] Patent Number: 5,942,229
[45] Date of Patent: Aug. 24, 1999

[54] METHOD FOR PROLONGED SUPPRESSION OF HUMORAL IMMUNE RESPONSE TO A THYMUS-DEPENDENT ANTIGEN THERAPEUTIC AGENT

[75] Inventors: Randolph J. Noelle, Cornish, N.H.; Teresa M. Foy, Seattle, Wash.

[73] Assignee: Trustees of Dartmouth College, Hanover, N.H.

[21] Appl. No.: 08/475,873

[22] Filed: Jun. 7, 1995

Related U.S. Application Data

[63] Continuation of application No. 08/115,990, Sep. 2, 1993, abandoned.

[51] Int. Cl.[6] ........................ A61K 39/395; A61K 38/17; A61K 35/12
[52] U.S. Cl. .................... 424/154.1; 424/130.1; 424/133.1; 424/134.1; 424/141.1; 424/143.1; 424/144.1; 424/153.1; 424/173.1; 424/185.1; 424/195.11; 514/2; 514/8; 514/885; 530/350; 530/387.1; 530/387.3; 530/388.1; 530/388.2; 530/388.22; 530/388.7; 530/388.73; 530/388.75
[58] Field of Search ........................ 424/130.1, 133.1, 424/141.1, 143.1, 144.1, 153.1, 154.1, 173.1, 134.1, 185.1; 514/48, 885; 530/350, 388.1, 388.7

[56] References Cited

U.S. PATENT DOCUMENTS 5,474,771  12/1995  Lederman et al. .................... 424/133.1

FOREIGN PATENT DOCUMENTS

| | | |
|---|---|---|
| 0 555 880 | 8/1993 | European Pat. Off. . |
| WO 93/08207 | 4/1993 | WIPO . |
| WO 93/09812 | 5/1993 | WIPO . |
| WO 94/04570 | 3/1994 | WIPO . |

OTHER PUBLICATIONS

Scaria et al. Gene Therapy 4: 611–617 (1997).
Datja Arthristis and Rheumatism 40: 1735–1745 (1997).
Allen et al. (1993) "CD40 Ligand Gene Defects Responsible for X–linked Hyper–lgM Syndrome" *Science* 259:990–993.
Armitage et al. (1992) "Molecular and biological characterization of a murine ligand for CD40" *Nature* 357:80–82.
Aruffo et al. (1990) "CD44 Is the Principal Cell Surface Receptor for Hyaluronate" *Cell* 61:1303–1313.
Aruffo et al. (1993) "The CD40 Ligand, gp39, Is Defective in Activated T Cells from from Patients with X–Linked Hyper–lgM Syndrome" *Cell* 72: 291–300.
Bartlett et al. (1990) "Cognate Interactions Between Helper T Cells and B Cells" *J. Immunol.* 145(12):3956–3962.
Chatterjee et al. (1994) "Idiotypic antibody immunotherapy of cancer" *Cancer Immunol. Immunother.* 38:75–82.
Dillman et al. (1989) "Monoclonal Antibodies for Treating Cancer" *Annals of Internal Medicine* 111(7): 592–603.
DiSanto et al. (1993) "CD40 ligand mutations in X–linked immunodeficiency with hyper–IgM" *Nature* 361:541–543.
Fanslow et al. (1992) "Soluble Forms of CD40 Inhibit Biologic Responses of Human B Cells" *Journal of Immunology* 149(2):655–660.
Fitch et al. (1993) "Cell Mediated Immune Regulation" *Fundamental Immunology*, 3rd Ed., William E. Paul (ed.) (New York: Raven Press Ltd.) Chp. 13:733, 735–737.
Foy et al. (1994) "gp39–CD40 Interactions Are Essential for Germinal Center Formation and Development of B Cell Memory" *J. Exp. Med.* 180: 157–163.
Foy et al. (1993) "In Vivo CD40–gp39 Interactions Are Essential for Thymus–dependent Humoral Immunity. II. Prolonged Suppression of the Hormoral Immune Response by an Antibody to the Ligand for CD40, gp39" *J. Exp. Med.* 178:1567–1575.
Harris et al. (1993) "Therapeutic antibodies—the coming of age" *Tibech* 11:42–44.
Hodgkin et al. (1990) "Separation of Events Mediating B Cell Proliferation and Ig Production By Using T Cell Membranes and Lymphokines" *J. Immunol.* 145(7):2025–2034.
Hollenbaugh et al. (1992) "The human T cell antigen gp39, a member of the TNF gene family, is a ligand for the CD40 receptor: expression of a soluble form of gp39 with B cell co–stimulatory activity" *EMBO Journal* 11(12):4313–4321.
Korthäuer et al. (1993) "Defective expression of T–cell CD40 ligand causes X–linked immunodeficiency with hyper–IgM" *Nature* 361:539–541.
Lane et al. (1992) "Activated human T cells express a ligand for the human B cell–associated antigen CD40 which particpates in T–cell–dependent activation of B lymphocytes" *Eur. J. Immunol.* 22:2573–2578.
Lederman et al (1992) "Identification of a Novel Surface Protein on Activated CD4[+] T Cells that Induces Contact–dependent B cell Differentiation (Help)" *J. Exp. Med.* 175: 1091–1101.
Lederman et al. (1992) "Molecular Interactions Mediating T–B Lymphocyte collaboration in Human Lymphoid Follicle" *J. Immunol.* 149(12):3817–3826.
Marshall et al. (1993) "The Molecular Basis for T Cell Help in Humoral Immunity: CD40 and Its Ligand, gp39" *J. Clin. Immunol.* 13(3): 165–174.
Mountain and Adair (1992) "Engineering Antibodies for Therapy" *Biotechnology and Genetic Engineering Reviews* 10:1, 10–13.
Noelle and Snow (1992) "T helper cells" Curr. Opin. Immunol 4:333–337.

(List continued on next page.)

Primary Examiner—Christina Y. Chan
Assistant Examiner—Phillip Gambel
Attorney, Agent, or Firm—Burns, Doane, Swecker & Mathis, L.L.P.

[57] ABSTRACT

Methods of suppressing a humoral immune response to a thymus-dependent (TD) antigen are disclosed. The methods involve administering to a subject a TD antigen with an antagonist of a molecule which mediates contact-dependent helper effector functions. In a preferred embodiment, the antagonist is an antagonist of gp39. Primary and secondary humoral immune responses can be suppressed and suppression is prolonged.

17 Claims, 6 Drawing Sheets

OTHER PUBLICATIONS

Noelle et al. (1992) "A 39–kDa protein on activated helper T cells binds CD40 and Transduces the signal for cognate activation of B cells" *PNAS USA* 89:6550–6554.

Noelle et al. (1992) "CD40 and its ligand, an essential ligand–receptor pair for thymus–dependent B–cell activation" *Immunology Today* 13:431–433.

Nossal (1989) "Immunologic Tolerance" in *Fundamental Immunology*, William E. Paul (ed.) (New York: Raven Press Ltd.) Chp. 19: 571–586.

Paulie et al. (1989) "The Human B Lymphocyte and Carcinoma Antigen, CDw40, is a Phosphoprotien Involved in Growth Signal Transduction" *J. Immunol.* 142: 590:595.

Spriggs et al. (1992) "Recombinant Human CD40 Ligand Stimulates B Cell Proliferation and Immunoglobulin E Secretion" *J. Exp. Med.* 176: 1543–1550.

Stamenkovic et al. (1989) "A B–lymphocyte activation molecule related to the nerve growth factor recptor and induced by cytokines in carcinomas" *EMBO Journal* 8(5):1403–1410.

Teale and Klinman (1984) "Control of the Production of Different Classes of Antibody" in *Fundamental Immunology*, William E. Paul (ed.) (New York: Raven Press Ltd.) Chp. 19:519–535.

Tueveson (1993) "New Immunosuppressants: Testing and Development in Animal Models and the Clinic: with Special Reference to DSG" *Immunological Reviews* 136:99–109.

Waldmann (1992) "Immune Receptors: Targets for Therapy of Leukemia/Lymphoma, Autoimmune Diseases and for the Preventiaon of Allograft Rejection" *Ann. Rev. Immunol.* 10:675–704.

Waldmann et al. (1991) "Monoclonal Antibodies in Diagnosis and Diagnosis and Therapy" *Science* 52:1657–1662.

Yellin et al. (1991) "A Human CD4–T Cell Leukemia Subclone with Contact–dependent Helper Function" *J. Immunol.* 147:3389–3395.

Gray et al. J. Exp Med 180: 141–155 (1994).

Stuber et al. J Exp Med. 183: 693–698 (1996).

Biacone et al. Kidney Intl. 48: 458–468 (1995).

Larsen et al. Transplantation 61: 4–9 (1996).

Rosen et al. Dictionary of Immunology Stockton Press NY NY 1989, p. 210 only.

METHOD FOR PROLONGED SUPPRESSION OF HUMORAL IMMUNE RESPONSE TO A THYMUS-DEPENDENT ANTIGEN THERAPEUTIC AGENT

This application is a continuation application of Ser. No. 08/115,990 filed on Sep. 2, 1993, now abandoned. The contents of the aforementioned application is hereby incorporated by reference.

GOVERNMENT FUNDING

The work leading to this invention may have been supported by one or more grants from the U.S. government. The U.S. government therefore may have certain rights in this invention.

BACKGROUND OF THE INVENTION

The immune system is capable of producing two types of antigen-specific responses to foreign antigen. Cell-mediated immunity is the term used to refer to effector functions of the immune system mediated by T lymphocytes. Humoral immunity is the term used to refer to production of antigen-specific antibodies by B lymphocytes. It has long been appreciated that the development of humoral immunity against most antigens requires not only antibody-producing B lymphocytes but also the involvement of helper T (hereafter Th) lymphocytes. Mitchison, *Eur. J. Immunol.*, 1:18–25 (1971); Claman and Chaperon, *Transplant Rev.*, 1:92–119 (1969); Katz et al., *Proc. Natl. Acad. Sci. USA*, 70:2624–2629 (1973); Raff et al., *Nature*, 226:1257–1260 (1970). Certain signals, or "help", are provided by Th cells in response to stimulation by thymus-dependent (hereafter TD) antigens. While some B lymphocyte help is mediated by soluble molecules released by Th cells (for instance lymphokines such as IL-4 and IL-5), activation of B cells also requires a contact-dependent interaction between B cells and Th cells. Hirohata et al., *J. Immunol.*, 140:3736–3744 (1988); Bartlett et al., *J. Immunol.*, 143:1745–1754 (1989). This indicates that B cell activation involves an obligatory interaction between cell surface molecules on B cells and Th cells. Such an interaction is further supported by the observation that isolated plasma membranes of activated T cells can provide helper functions necessary for B cell activation. Brian, *Proc. Natl. Acad. Sci. USA*, 85:564–568 (1988); Hodgkin et al., *J. Immunol.*, 145:2025–2034 (1990); Noelle et al., *J. Immunol.*, 146:1118–1124 (1991).

A cell surface molecule, CD40, has been identified on immature and mature B lymphocytes which, when crosslinked by antibodies, induces B cell proliferation. Valle et al., *Eur. J. Immunol.*, 19:1463–1467 (1989); Gordon et al., *J. Immunol.*, 140:1425–1430 (1988); Gruber et al., *J. Immunol.*, 142: 4144–4152 (1989). CD40 has been molecularly cloned and characterized. Stamenkovic et al., *EMBO J.*, 8:1403–1410 (1989). A ligand for CD40, gp39 (also called CD40 ligand or CD40L) has also been molecularly cloned and characterized. Armitage et al., *Nature*, 357:80–82 (1992); Lederman et al., *J. Exp. Med.*, 175:1091–1101 (1992); Hollenbaugh et al., *EMBO J.*, 11:4313–4319 (1992). The gp39 protein is expressed on activated, but not resting, CD4$^+$ Th cells. Spriggs et al., *J. Exp. Med.*, 176:1543–1550 (1992); Lane et al., *Eur. J. Immunol.*, 22:2573–2578 (1992); Roy et al., *J. Immunol.*, 151:1–14 (1993). Cells transfected with the gp39 gene and expressing the gp39 protein on their surface can trigger B cell proliferation and, together with other stimulatory signals, can induce antibody production. Armitage et al., *Nature*, 357:80–82 (1992); Hollenbaugh et al., *EMBO J.*, 11:4313–4319 (1992).

While the induction of a humoral immune response is an important host defense mechanism, in certain situations it would be beneficial to suppress antibody production against a particular antigen. For example, suppression of a humoral response against an allergen could prevent or reduce an allergic response in an individual. Additionally, when a therapeutic antibody is administered, suppressing a humoral response against the antibody could prolong the therapeutic efficacy of the antibody.

SUMMARY OF THE INVENTION

One approach to suppressing humoral immunity is to inhibit B cell activation. The current invention pertains to methods for inhibiting a humoral immune response to a TD antigen in vivo by inhibiting the ability of a Th cell to stimulate a B cell, thereby interfering with B cell activation and antibody production. The invention is based, at least in part, on the necessity for an in vivo interaction between gp39 on a Th cell and CD40 on a B cell for subsequent activation of the B cell. Antagonists of gp39, which are effective for inhibiting the interaction of gp39 with CD40 in vivo, are administered to a subject together with a TD antigen to suppress humoral immunity against the TD antigen. The gp39 antagonist which is administered can be an antibody directed against gp39. In a preferred embodiment, the gp39 antagonist is a monoclonal antibody, such as a anti-human gp39 antibody or an anti-mouse gp39 antibody (e.g., MR1). Chimeric antibodies, humanized antibodies and antibody fragments are also within the scope of the invention. Alternatively, the gp39 antagonist can be a soluble form of the gp39 ligand CD40. Soluble fusion proteins of CD40 are also encompassed by the invention.

The humoral immune response inhibited by the methods of the current invention can be a primary humoral immune response, in the case of initial exposure to an antigen, or a secondary humoral immune response, in the case of reexposure to a previously encountered antigen. For example, the methods described herein can be used to inhibit production of antigen-specific IgM antibodies, IgG antibodies, IgD antibodies and/or IgE antibodies. In addition, the methods provide for prolonged suppression of humoral immune responses in vivo.

One aspect of the invention provides methods for inhibiting humoral immune responses to TD antigens. Antigens embraced by the invention include antigens for which specific antibody production requires interaction of gp39 with a ligand on the surface of B cells (e.g., CD40). TD antigens generally include proteinaceous antigens. In preferred embodiments of the invention, the antigen is a therapeutic antibody, drug, allergen or foreign cell. The methods of the present invention also are effective for inhibiting humoral immune responses to a TD antigen while preserving humoral immune responses to thymus-independent type II (hereafter TI-2) antigens.

Another aspect of the invention pertains to methods for specifically inhibiting the helper function of activated Th cells in vivo by interfering with the interaction of gp39 with a ligand on the surface of B cells (e.g., CD40) by administering a gp39 antagonist. According to this method, helper function of activated Th cells is inhibited in vivo without deleting or anergizing Th cells.

The invention further pertains to methods of inhibiting humoral immune responses in vivo by a combined administration of a gp39 antagonist and another immunosuppressive agent. Other immunosuppressive agents which can be provided in conjunction with a gp39 antagonist include cytokine inhibitors, inhibitors of the CD28/CTLA4 T cell costimulatory pathway, or immunosuppressive drugs.

A still further aspect of the present invention is a method for determining whether an antigen is a TD or TI-2 antigen. This can be determined by whether or not humoral immune responses to the antigen in vivo can be inhibited by administration of a gp39 antagonist.

DETAILED DESCRIPTION OF THE INVENTION

Figure 1A:
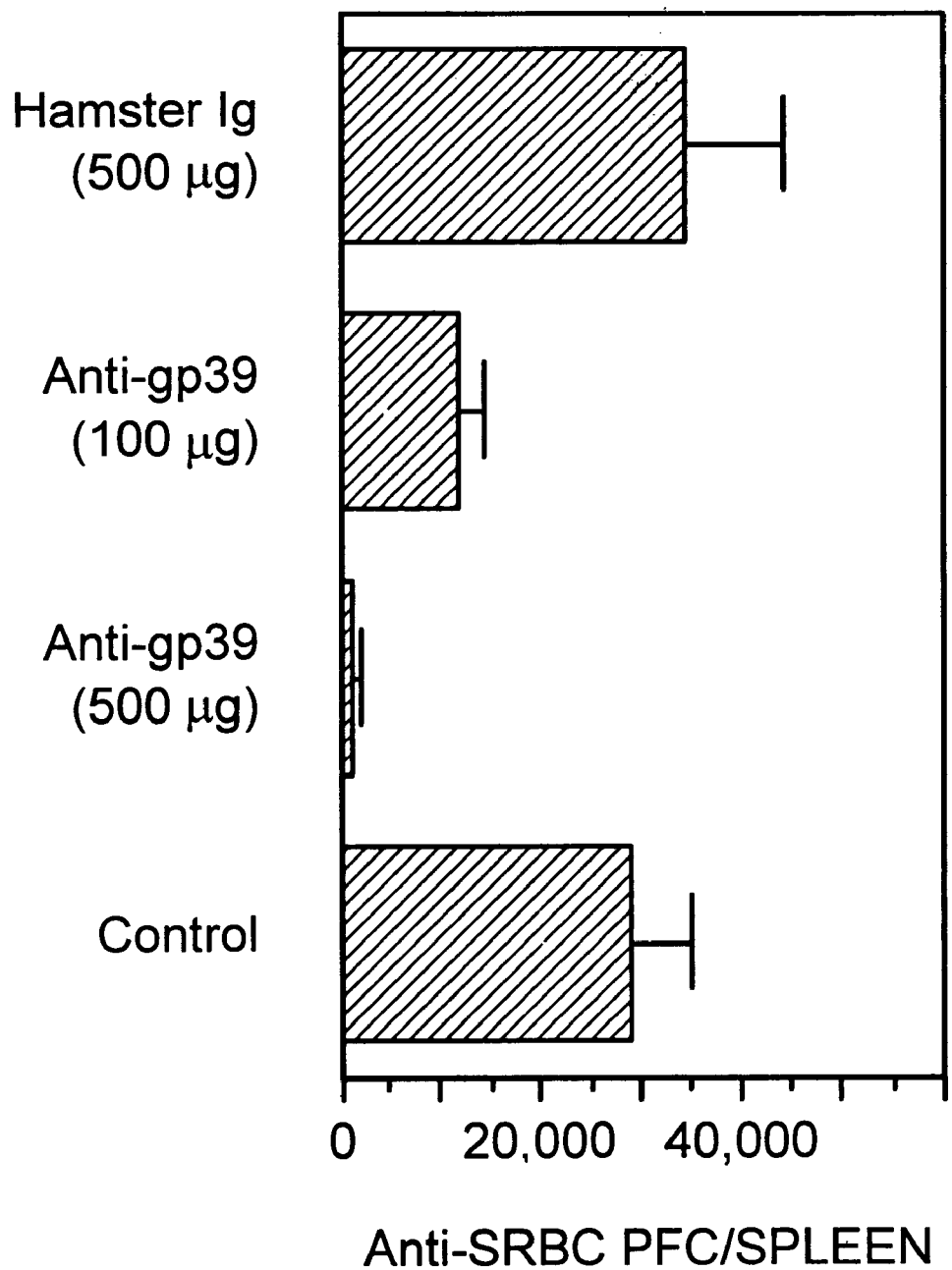
FIG. 1A is a bar graph depicting suppression of primary anti-SRBC IgM antibody production by in vivo anti-gp39 treatment.

The generation of humoral immunity to thymus-dependent (TD) antigens requires not only B lymphocytes, which can produce specific antibodies against an antigen, but also contributions from Th cells which are necessary for activation of B lymphocytes. Although T helper cell function does involve production of cytokines utilized by B lymphocytes, the Th cell requirement for B cell activation cannot be eliminated by providing exogenous cytokines to B cells. Rather, a contact-dependent, cell membrane-mediated interaction between B cells and Th cells is integral to induction of humoral responses. A receptor-ligand pair involved in this interaction, CD40 and gp39, has been identified. CD40 is present on B cells and has the ability to bind to gp39, which is induced on Th cells upon activation, leading to stimulation of the B cells and ultimately production of specific antibodies. Disruption of the CD40-gp39 interaction offers a means of interfering with the generation of a specific humoral immune response.

Accordingly, this invention pertains to methods of inhibiting humoral immune responses against a TD antigen in vivo. Humoral immune responses are inhibited by interfering with the interaction of a molecule on a Th cell which mediates contact-dependent helper effector function and it's ligand on the surface of a B lymphocyte. In a preferred embodiment, humoral immune responses are inhibited by interfering with the interaction of gp39 on a T cell and CD40 on a B cell exposed to the TD antigen through administration of a gp39 antagonist to a subject in vivo. In one embodiment, the B cell is exposed to the TD antigen by administration of the antigen in vivo with the gp39 antagonist. Preferably, this TD antigen is a therapeutic agent, for example a therapeutic antibody or drug, which is administered to the patient for therapeutic treatment and for which inhibiting humoral immune responses against it can result in prolonged therapeutic efficacy of the agent. In another embodiment, the TD antigen is an antigen to which a subject is exposed to environmentally, for example an allergan, in which a humoral immune response is detrimental to the subject, for example results in an allergic reaction. Inhibition of a humoral immune response in this situation would be therapeutically beneficial to the subject.

I. GP39 ANTAGONISTS

According to the methods of the invention, a gp39 antagonist is administered to a subject to interfere with the interaction of gp39 on T cells with a gp39 ligand on B cells. A gp39 antagonist is defined as a molecule which interferes with this interaction. The gp39 antagonist can be an antibody directed against gp39 (e.g., a monoclonal antibody against gp39), fragments or derivative of an antibody directed against gp39 (e.g., Fab or F(ab)'2 fragments, chimeric antibodies or humanized antibodies), soluble forms of a gp39 ligand (e.g., soluble CD40), soluble forms of a fusion protein of a gp39 ligand (e.g., soluble CD40Ig), or pharmaceutical agents which disrupt the gp39-CD40 interaction.

A. Antibodies

A mammal, (e.g., a mouse, hamster, or rabbit) can be immunized with an immunogenic form of gp39 protein or protein fragment (e.g., peptide fragment) which elicits an antibody response in the mammal. A cell which expresses gp39 on its surface can also be used as the immunogen. Alternative immunogens include purified gp39 protein or protein fragments. gp39 can be purified from a gp39-expressing cell by standard purification techniques; gp39 cDNA (Armitage et al., *Nature*, 357:80–82 (1992); Lederman et al., *J. Exp. Med.*, 175:1091–1101 (1992); Hollenbaugh et al., *EMBO J.*, 11:4313–4319 (1992)) can be expressed in a host cell, e.g. bacteria or a mammalian cell line, and gp39 protein purified. gp39 peptides can be synthesized based upon the amino acid sequence of gp39 (Armitage et al., *Nature*, 357:80–82 (1992); Lederman et al., *J. Exp. Med.*, 175:1091–1101 (1992); Hollenbaugh et al., *EMBO J.*, 11:4313–4319 (1992)). Techniques for conferring immunogenicity on a protein include conjugation to carriers or other techniques well known in the art. For example, the protein can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* (1975) 256:495–497) as well as other techniques such as the human B-cell hybridoma technique (Kozbar et al., *Immunol. Today* (1983) 4:72), the EBV-hybridoma technique to produce human monoclonal antibodies (Cole et al. *Monoclonal Antibodies in Cancer Therapy* (1985) (Allen R. Bliss, Inc., pages 77–96), and screening of combinatorial antibody libraries (Huse et al., *Science* (1989) 246:1275). Hybridoma cells can be screened immunochemically for production of antibodies specifically reactive with the protein or peptide and monoclonal antibodies isolated.

The term antibody as used herein is intended to include fragments thereof which are also specifically reactive with gp39 protein or peptide thereof or gp39 fusion protein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-gp39 portion.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes gp39. See, for example, Morrison et al., *Proc. Natl. Acad. Sci. U.S.A.* 81:6851 (1985); Takeda et al., *Nature* 314:452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. It is expected that such chimeric antibodies would be less immunogenic in a human subject than the corresponding non-chimeric antibody.

For human therapeutic purposes the monoclonal or chimeric antibodies specifically reactive with a gp39 protein or peptide can be further humanized by producing human constant region chimeras, in which parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., *Proc. Natl. Acad. Sci. U.S.A.*, 80:7308–7312 (1983); Kozbor et al., *Immunology Today*, 4:7279 (1983); Olsson et al., *Meth. Enzymol.*, 92:3–16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain.

Another method of generating specific antibodies, or antibody fragments, reactive against a gp39 protein or peptide is to screen expression libraries encoding immunoglobulin genes, or portions thereof, expressed in bacteria with a gp39 protein or peptide. For example, complete Fab fragments, VH regions and Fv regions can be expressed in bacteria using phage expression libraries. See for example Ward et al., *Nature*, 341: 544–546: (1989); Huse et al., *Science*, 246: 1275–1281 (1989); and McCafferty et al., *Nature*, 348: 552–554 (1990). Screening such libraries with, for example, a gp39 peptide can identify imunoglobin fragments reactive with gp39. Alternatively, the SCID-hu mouse developed by Genpharm can be used to produce antibodies, or fragments thereof.

For suppression of humoral immune responses in a human subject, it is preferable to administer an antibody directed against human gp39. The following methodology was used to produce mouse anti-human gp39 monoclonal antibodies.

BALB/C mice were immunized with a soluble gp39 fusion protein, gp39-CD8, in Complete Freund's Adjuvant (CFA). Mice were subsequently challenged 6 weeks later with soluble gp39-CD8 in Incomplete Freund's Adjuvant (JFA). Soluble gp39-CD8 was given in soluble form 4 weeks after secondary immunization. Mice were then boosted with activated human peripheral blood lymphocytes 2 weeks later, followed by a final boost with soluble gp39-CD8 after an additional 2 weeks. Splenocytes were fused with the NS-1 fusion partner on day 4 after final immunization as per standard protocols.

Clones producing anti-human gp39 antibodies were selected based on a multiple screening process. Clones were initially screened by a plate binding assay using gp39-CD8. Positive clones were then screened against a control CD8 fusion protein, CD72-CD8. Clones which scored positive on the CD8-CD72 plate binding assay were eliminated. The remaining clones were subsequently screened on resting and 6 hour activated human peripheral blood lymphocytes (PBL) by flow cytometric analysis. Hybridomas staining activated, but not resting, PBL were considered positive. Finally, the remaining clones were tested for their ability to block the binding of CD40Ig to plate bound gp39.

Approximately 300 clones were initially screened against gp39-CD8 and CD72-CD8 in the plate binding assays. Of those clones, 30 were found to detect plate-bound gp39 and not CD8. These clones were subsequently screened for detection of gp39 on activated human PBL. Approximately 15 clones detected a molecule on activated PBL, but not resting cells. Specificity was further confirmed by determining the capacity of the clones to block CD40Ig detection of plate-bound gp39. 3 of 10 clones tested block CD40Ig binding in this assay. These clones were 3E4, 2I5 and 2I8. Such clones are preferred for use in the methods described herein. Clones which tested positive on activated, but not resting PBL, were also screened for reactivity with an activated rat T cell clone, POMC8. The clone 2H8 expressed crossreactivity with this rat T cell line.

In a preferred embodiment of the invention, the gp39 antagonist is a anti-mouse gp39 monoclonal antibody, MR1. The following method was used to produce the MR1 monoclonal antibody, and may be used to generate other antibodies directed toward gp39.

Hamsters were immunized intraperitoneally with 5–10$^6$ activated T$_h$1 cells (d1.6) at weekly intervals for six weeks. When the serum titer against murine T$_h$1 was greater than about 1:10,000, cell fusions were performed with polyethylene glycol using immune hamster splenocytes and NSI. SN from wells containing growing hybridomas were screened by flow cytometry on resting and activated $T_h1$. One particular hybridoma, which produced a Mab that selectively recognized activated $T_h$ was further tested and subcloned to derive MR1. MR1 was produced in ascites and purified by ion exchange HPLC. A hybridoma MR1 has been deposited with the American Type Culture Collection and assigned Accession Number HB11048.

B. Soluble Ligands for gp39

Other gp39 antagonists which can be administered to suppress humoral immunity are soluble forms of a gp39 ligand. A monovalent soluble ligand of gp39 can bind gp39, thereby inhibiting the interaction of gp39 with CD40 on B cells. The term soluble indicates that the ligand is not permanently associated with a cell membrane. A soluble gp39 ligand can be prepared by chemical synthesis, or, preferably by recombinant DNA techniques. A preferred soluble gp39 ligand is soluble CD40. Alternatively, soluble gp39 ligand can be in the form of a fusion protein. Such a fusion protein comprises at a least a portion of the gp39 ligand attached to a second molecule. For example, CD40 can be expressed as a fusion protein with immunoglobulin (CD40Ig). In one embodiment, a fusion protein is produced comprising a amino acid residues of an extracellular domain portion of the CD40 joined to amino acid residues of a sequence corresponding to the hinge, CH2 and CH3 regions of Cγ1 to form a CD40Ig fusion protein (see e.g., Linsley et al. (1991) *J. Exp. Med.* 1783:721–730; Capon et al. (1989) *Nature* 337, 525–531; and Capon U.S. 5,116,964). The fusion protein can be produced by chemical synthesis, or, preferably by recombinant DNA techniques based on the cDNA of CD40 (Stamenkovic et al., *EMBO J.*, 8:1403–1410 (1989)).

II.ANTIGENS AGAINST WHICH HUMORAL IMMUNITY IS SUPPRESSED

The invention is directed to suppressing humoral immunity against antigens which require contact-dependent helper functions delivered by Th cells. Antigens classically described as thymus-dependent (TD) antigens are encompassed by the invention. The necessity for contact-dependent "help" from Th cells can be due to the necessity for an interaction between gp39 on T cells and CD40 on B cells. As defined by the current invention, the term "TD antigen" is intended to encompass antigens which require a gp39-CD40 interaction between T cells and B cells for induction of a humoral immune response against the antigen. In general, protein antigens are TD antigens. Another form of TD antigen encompassed by the invention is a molecule, referred to as a hapten, linked to a protein. In this case, the protein acts as a carrier for inducing T cell help in order to induce humoral immune responses against the hapten.

The TD antigen of the invention can be administered in soluble form to a subject, e.g., injection of a soluble protein, or the TD antigen can be on the surface of a cell, e.g., a cell-surface protein. The TD antigen can be administered to a subject with a gp39 antagonist or a subject may be exposed to a TD antigen environmentally, for example an allergen. In preferred embodiments, the TD antigen is an agent administered to a subject for therapeutic purposes. This agent can be, for example, a therapeutic antibody or other form of therapeutic drug which is a TD antigen. Inhibiting a humoral immune response against, for instance, a therapeutic antibody, can prolong its efficacy in vivo by preventing clearance of the therapeutic antibody in a subject. Small molecules acting as therapeutic agents can also be target antigens against which a humoral response is suppressed if these molecules (functioning as haptens) are administered with a protein or other carrier that induces T cell helper function to activate B cells; suppressing humoral immunity against these therapeutic agents can likewise prolong their effectiveness.

The methods of the invention provide for suppression of humoral immunity against TD antigens while not affecting responses to thymus-independent type II (TI-2) antigens. TI-2 antigens include polysaccharides and lipids which can non-specifically activate B cells in a polyclonal manner. As defined by the current invention, the term "TI-2 antigen" is intended to encompass all antigens which do not require a gp39-CD40 interaction between T cells and B cells for induction of a humoral immune response against the antigen. The current invention provides a method for identifying whether an antigen is a TD antigen or a TI-2 antigen, as defined in the invention, by determining whether humoral immune responses to the antigen can be inhibited by a gp39 antagonist.

III. SUPPRESSION OF HUMORAL IMMUNITY

The invention pertains to methods of inhibiting a humoral immune response against a TD antigen. The humoral immune response can be a primary immune response, in the case of a first exposure to a TD antigen, or the response can be a secondary humoral immune response, in the case of reexposure to the antigen. Production of one or more isotypes of antibodies can be inhibited. For a primary humoral immune response, in which IgM is the predominant antibody produced, IgM production is predominantly suppressed. For secondary immune response, production of several different isotypes, incuding IgM, IgG and IgE can be suppressed.

The invention provides methods for prolonged suppression of humoral immunity against a TD antigen. As used herein, "prolonged suppression" means that suppression of antibody production against a TD antigen is maintained after administration of a gp39 antagonist in vivo has been terminated.

IV. ADMINISTRATION OF GP39 ANTAGONISTS

Humoral immune responses to a TD antigen can be inhibited according to the methods described herein by administration of a gp39 antagonist to a subject which is exposed to the TD antigen. In one embodiment, the gp39 antagonist is administered in conjunction with the TD antigen. The gp39 antagonist is preferably administered simultaneously with the TD antigen, but can be administered prior to administering the TD antigen or subsequent to the TD antigen, as long as the gp39 antagonist is administered before the TD antigen has induced B cell activation. In other embodiments, a subject is exposed to an antigen environmentally. In this case, a gp39 antagonist should be administered in vivo following exposure to the antigen, in close enough in time to prevent B cell activation.

The antagonists of the invention are administered to subjects in a biologically compatible form suitable for pharmaceutical administration in vivo to suppress humoral immune responses. By "biologically compatible form suitable for administration in vivo" is meant a form of the antagonist to be administered in which any toxic effects are outweighed by the therapeutic effects of the protein. The term subject is intended to include living organisms in which an immune response can be elicited, e.g., mammals. Examples of subjects include humans, dogs, cats, mice, rats, and transgenic species thereof. Administration of an antagonist which interferes with the interaction of gp39 and CD40 as described herein can be in any pharmacological form and a pharmaceutically acceptable carrier. Administration of a therapeutically active amount of the therapeutic compositions of the present invention is defined as an amount effective, at dosages and for periods of time necessay to achieve the desired result. For example, a therapeutically active amount of an antagonist which interferes with the interaction of gp39 and CD40 may vary according to factors such as the disease state, age, sex, and weight of the individual, and the ability of the antagonist to elicit a desired response in the individual. Dosage regima may be adjusted to provide the optimum therapeutic response. For example, several divided doses may be administered daily or the dose may be proportionally reduced as indicated by the exigencies of the therapeutic situation.

The active compound (e.g., antagonist) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

To administer an antagonist which interferes with the interaction of gp39 and CD40 by other than parenteral administration, it may be necessary to coat the antagonist with, or co-administer the antagonist with, a material to prevent its inactivation. For example, an antagonist can be administered to an individual in an appropriate carrier or diluent, co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., antagonist which interferes with the interaction of gp39 and CD40) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., antagonist) plus any additional desired ingredient from a previously sterile-filtered solution thereof.

When the active compound is suitably protected, as described above, the protein may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

V. COADMINISTRATION OF GP39 ANTAGONISTS AND OTHER IMMUNOSUPPRESSIVE AGENTS

It has been shown that the interference by soluble CTLA-4 of CD28 triggering, a co-stimulatory molecule on Th cells, also suppresses TD antibody responses (30) and blocks xenogeneic graft rejection (31). Similar to anti-gp39 administration, soluble CTLA-4 induced a state of prolonged immune suppression. Because anti-gp39 and CTLA-4 mediate their immunosuppressive effects at distinct stages of the humoral immune response, co-administration of these two immunosuppressive drugs may provide additive or synergistic immunosuppressive effects on immunity.

Allergic responses are mediated by IgE antibodies. The production of IgE responses requires the cytokine IL-4.

Inhibition of IgE responses against a TD antigen may be more efficient by coadministration of a gp39 antagonist and an inhibitor of IL-4, for example an anti-IL-4 antibody.

This invention is further illustrated by the following examples which should not be construed as limiting. The contents of all references and published patent applications cited throughout this application are hereby incorporated by reference. The contents of a patent application filed on even date herewith in the name of Randolph J. Noelle et al. and entitled "Methods for Inducing Antigen-Specific T Cell Tolerance" is incorported herein by reference.

The following methodology was used in the examples.

Materials and Methods

Animals. Female, 6–8 week old BALB/C mice (Jackson Laboratories, Bar Harbor, Me.) were used for the in vivo experiments presented in this study. Animals were maintained in the specific pathogen-free animal facility at Dartmouth Medical School.

Helper T cell clones ($T_h1$). D1.6, an $I-A^d$-restricted, rabbit Ig-specific $T_h1$ clone (21) was obtained from Dr. David Parker, University of Mass. at Worcester. In this paper, D1.6 will be referred to as $T_h1$.

Reagents and Antibodies. MR1, hamster anti-murine gp39 mAb (16) was purified by DEAE HPLC from ascites fluid. Hamster Ig (HIg), used as a control antibody, was purified similarly from hamster serum (Accurate Chemical and Scientific Corp., Westbuty, N.Y.). RG7/7.6. HL, a mouse anti-rat κ chain (strongly crossreactive with hamster κ chain) antibody, (RG7), (22) was conjugated with HRPO or FITC and used as a secondary reagent to detect MR1 and HIg. Affinity-purified Goat anti-mouse IgM, $IgG_1$, $IgG_{2a}$, $IgG_{2b}$ and $IgG_3$ (Southern Biotechnology, Birmingham Ala.) were used as detection antibodies in the antigen specific ELISAs as well as in the total IgM and $IgG_1$ ELISAs. B1E3, (kindly provided by Dr. T. Waldschmidt, Univ. of Iowa) a monoclonal anti-murine IgE, was used as the detection antibody for the IgE anti-KLH ELISA. Chimeric-L6 (Chi-L6), a humanized $IgG_1$ specific for the tumor antigen L6 (23), was kindly provided by Bristol-Myers Squibb Pharmaceutical Research Institute, Seattle Wash. Anti-CD4, GK 1.5 (24) was prepared by HPLC purification of ascites fluid. Sheep red blood cells (SRBC) were purchased from Colorado Serum Co. (Denver, Colo.). Sea Plaque agarose for use in anti-SRBC plaque assay was obtained from FMC Corporation (Rockland Mass.). Baby rabbit complement was purchased from Cedarlane (Homby, Ontario Canada). KLH, Keyhole limpet hemocyanin, (from *Megathura crenulata*) was purchased from Calbiochem (LaJolla, Calif.). Complete Freund's adjuvant (CFA) for immunizations was obtained from Sigma Chemical Co (St. Louis, Mo.). TNP-SRBC, TNP-KLH and TNP-BSA were prepared as previously described (25).

Immunizations for Generation of In Vivo Primary and Secondary Antibody Responses.

Primary Immune Responses. For eliciting primary antibody responses to SRBC or TNP-SRBC, mice were immunized with 200 μl of 1% SRBC or TNP-SRBC suspension (i.v.). The IgM, anti-SRBC response was assayed 5d after administration of antigen using a modification of the Jerne plaque assay (26). IgM anti-TNP responses were measured by ELISA on day 6. Primary responses to the heterologous immunoglobulin Chi-L6 were generated by i.p. immunization of 100 μg Chi-L6 on alum per mouse. The serum IgM anti-Chi-L6 antibody response was measured after 7d. Primary responses to TNP-Ficoll were generated by immunization with 25 μg of TNP-Ficoll i.p. The IgM anti-TNP response was measured on day 6 by ELISA.

Secondary Immune Responses. For generation of secondary humoral responses to KLH, animals were immunized with KLH in CFA (50 μg; i.p.). Mice were subsequently challenged with 10 μg of soluble KLH (i.p.) three months later. The anti-KLH antibody response was measured on d7 from the serum of immune mice utilizing isotype specific ELISAs. Secondary antibody responses to Chi-L6 were generated by challenging Chi-L6 immune mice with 10 μg soluble Chi-L6, i.p. The serum $IgG_1$ anti-Chi-L6 antibody response was measured after 7d.

Anti-gp39 Treatment. Sterile, HPLC-purified anti-gp39 (MR1) or HIg (as an antibody control) was administered (i.p.) on d0, d2, d4 post immunization or challenge as indicated for each experiment.

Antigen Specific ELISAs. The antigen specific IgM, $IgG_1$, $IgG_{2a}$, $IgG_{2b}$, $IgG_3$, and IgE antibody titers were determined using isotype specific ELISAs. Briefly, antigen, (1 mg/ml of KLH, Chi-L6, $TNP_{16}$-BSA, or $TNP_2$-BSA in PBS) was absorbed onto flexible polyvinyl microtiter dishes, overnight at 4° C. Plates were washed and blocked with PBS-1% FCS-sodium-azide. Diluted serum samples were incubated for 2 hours at 37° C. Samples were washed and the antigen specific antibody titers determined with one of the following alkaline-phosphatase conjugated detection antibodies: goat anti-mouse IgM, $IgG_1$, $IgG_{2a}$, $IgG_{2b}$, or $IgG_3$ (Southern Biotechnology, Birmingham, Ala.). The IgE specific ELISA was detected using biotin-conjugated B1E3 followed by alkaline-phosphatase avidin (South San Francisco, Calif.). All ELISAs were developed by reaction of alkalinephosphatase with phosphatase substrate (Sigma Chemical, Co., St. Louis, Mo.). Plates were analyzed on a Dynatech MR700 ELISA reader at 410 nm. Units represent arbitrary values based on the titration curve of a standard immune serum. All experimental groups were titered from 1:100 to 1:100,000 and the titer ascertained based on multiple point analysis. The levels of anti-KLH, anti-Chi-L6 and anti-TNP antibodies in unchallenged controls were below detection.

Detection of Serum Anti-gp39.

Quantitation of intact anti-gp39 in the serum of anti-gp39-treated mice: Serum from mice receiving 750 μg anti-gp39 (250 μg on d0, d2, d4) was obtained on d7, d14, and d21 after initiation of anti-gp39 treatment. The serum was run on a 7.5% SDS gel under non-reducing conditions, transferred to nitrocellulose, and blotted with HRPO-conjugated RG7. Following chemiluminescent detection, areas of the blot corresponding to 150–165 kDa were scanned and digitized using an Apple Scanner and the Image 4.1 software program.

Analysis for biologically active anti-gp39 in the serum of treated mice: Anti-CD3-activated $T_h1$, which express gp39, were stained with dilutions of serum from mice receiving 750 μg anti-gp39 (250 μg on d0, d2, d4) to determine the amount of biologically active gp39 remaining in the serum. Titrations of serum containing anti-gp39 were incubated with activated $T_h1$ cell clones for 30 minutes at 4° C., followed by washing and subsequent incubation with FITC-RG7 for 30 minutes at 4° C. A standard curve of MFI vs anti-gp39 concentration was generated using purified anti-gp39. Samples were analyzed on a Becton Dickinson FAC-Scan and the percent anti-gp39 remaining in the serum was deduced based on the anti-gp39 standard curve. The level of anti-gp39 present in the serum at d7 was set at 100%.

Adoptive Transfer of Helper T cells. Mice were immunized with SRBC (200 μl of 1% SRBC, i.v.) and administered anti-gp39 or HIg (250 μg on d0, d2, d4). On d7 the splenocytes from nonimmune or SRBC-immune mice were removed, erythrocyte depleted, washed and transferred (i.v., 50×10$^6$/mouse) into irradiated recipients (600 rads) with or without 50×10$^6$ spleen cells from TNP-KLH primed (TNP-KLH-CFA, 50 µg i.p.) mice as a source of immune B cells. At the time of transfer, mice were immunized with TNP-SRBC (200 µl of 1% TNP-SRBC i.v.) Serum IgG$_1$ anti-TNP titers were ascertained on d6 post-transfer.

EXAMPLE 1

Anti-gp39 Inhibits the Generation of Primary Antibody Responses to Erythrocyte Antigens The impaired TD immunity observed in patients with HIM, as well as the potent inhibitory effects of anti-gp39 and CD40-Ig on $T_h$-dependent B cell activation in vitro, provided the basis for the study of the potential immunosuppressive effects of anti-gp39 on humoral-mediated immunity in vivo. To investigate the role of gp39-CD40 interactions in primary TD humoral immune responses, the effect of in vivo administration of anti-gp39 on the primary antibody response to sheep red blood cells (SRBC) was determined. Animals were immunized with SRBC and administered anti-gp39 mAb (or control HIg) over the course of 4d. On d5, the primary anti-SRBC antibody response of anti-gp39-treated, HIg-treated, and control mice was ascertained The IgM anti-SRBC plaque-forming cell (PFC) response of mice that received a total of 1.5 mg of anti-gp39 (500 µg/mouse on d0, d2 and d4) was reduced 99% when compared to the anti-SRBC PFC response from control or HIg-treated mice (FIG. 1A). In addition, administration of as little as 300 µg/mouse (100 µg/mouse on d0, d2, and d4) of anti-gp39 reduced the anti-SRBC primary immune response by 66%. Results from these experiments demonstrate that anti-gp39 treatment ablates primary antibody responses in vivo.

Figure 1B:
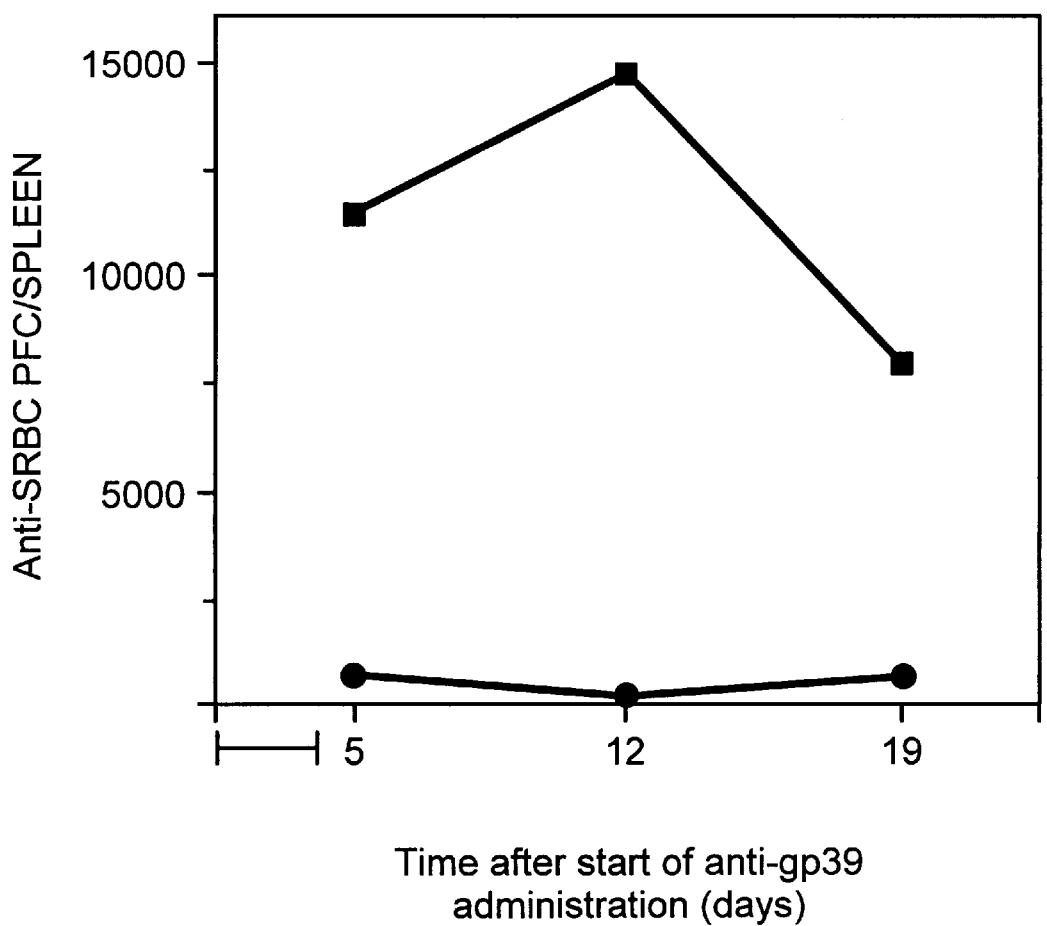
FIG. 1B is a graph depicting prolonged suppression of primary anti-SRBC IgM antibody production after short-term in vivo anti-gp39 treatment.

The duration of the immunosuppressive effects of anti-gp39 on the primary humoral immune response to SRBC was subsequently examined. Mice immunized with SRBC were treated with anti-gp39 for 4d and assayed at various later time points for the capacity to mount a primary anti-SRBC response. In this set of experiments, all animals were immunized with SRBC on d0 and administered anti-gp39 or HIg on d0, d2, d4. The IgM anti-SRBC PFC response was measured for one group on d5. Additional SRBC-immune groups were challenged with SRBC on d7 or d14. Five days following the each antigenic challenge (d12 and d19, respectively), the IgM anti-SRBC PFC response was measured. The results of one such experiment are depicted in FIG. 1B. As in FIG. 1A, the primary anti-SRBC responses were inhibited 80–90% 5d after anti-gp39 administration was begun. In addition, the primary anti-SRBC responses 12d and 19d following anti-gp39 treatment were also inhibited >90%. These results demonstrate that brief anti-gp39 treatment results in prolonged inhibition of primary antibody responses.

EXAMPLE 2

Anti-gp39 Inhibits the Generation of Secondary Anti-KLH Antibody Responses

Experiments examining primary antibody responses suggest that gp39-CD40 interactions play a critical role in the initiation of primary humoral immunity. However, these experiments do not address the whether gp39-dependent CD40 signalling is required for the generation of secondary antibody responses. Therefore, the effects of anti-gp39 administration on the secondary immune response to soluble challenge with KLH was determined in KLH-immune mice.

Figure 2A:
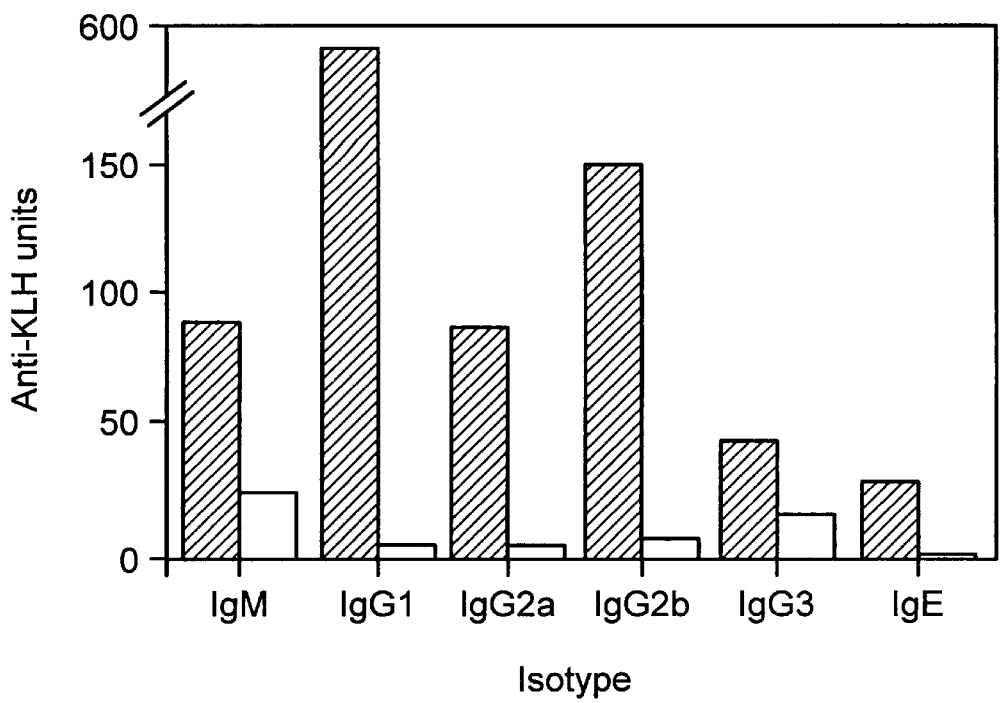
FIG. 2A is a bar graph depicting suppression of secondary anti-KLH antibody production (various isotypes) by in vivo anti-gp39 treatment. Antibody titers were measured 7 days after antigen challenge.
Figure 2B:
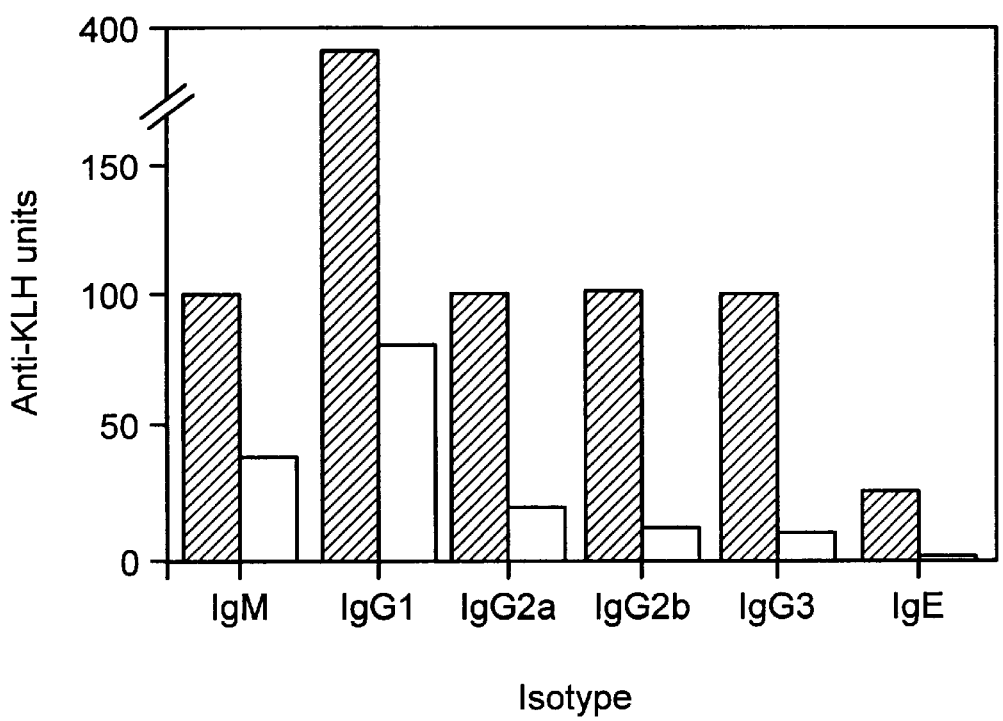
FIG. 2B is a bar graph depicting suppression of secondary anti-KLH antibody production (various isotypes) by in vivo anti-gp39 treatment. Antibody titers were measured 14 days after antigen challenge.

Using schedules of anti-gp39 administration that reduced the primary anti-SRBC PFC response, experiments were designed to evaluate the effects of anti-gp39 treatment on the secondary antibody responses. In these experiments, KLH-immune mice (immunized 3 months prior with CFA and KLH) were challenged with soluble KLH (10 µg/mouse/i.v.). On the day of antigen challenge (d0), mice were also given 250 µg of anti-gp39 or HIg, followed by anti-gp39 or HIg on d2 and d4. At d7 (FIG. 2 panel A) and d14 (FIG. 2 panel B) following challenge with KLH, the mice were bled and the titers of IgM, IgG$_1$, IgG$_{2a}$, IgG$_{2b}$, IgG$_3$ and IgE anti-KLH antibodies were determined. The results demonstrate several points: 1) challenge with soluble KLH induced an enduring secondary immune response that persisted for up to 14d; 2) the administration of anti-gp39 significantly reduced the secondary anti-KLH response of the isotypes measured when compared to the administration of equal quantities of HIg; and 3) the immunosuppressive effects of anti-gp39 appeared to be sustained for at least 14d after the initiation of anti-gp39 treatment. Taken together, results from these experiments demonstrate that similar to primary humoral immune responses, the generation of secondary humoral immune responses were also blocked by anti-gp39.

EXAMPLE 3

Anti-gp39 Inhibits the Generation of Antibody Responses to Heterologous Ig

Figure 3A:
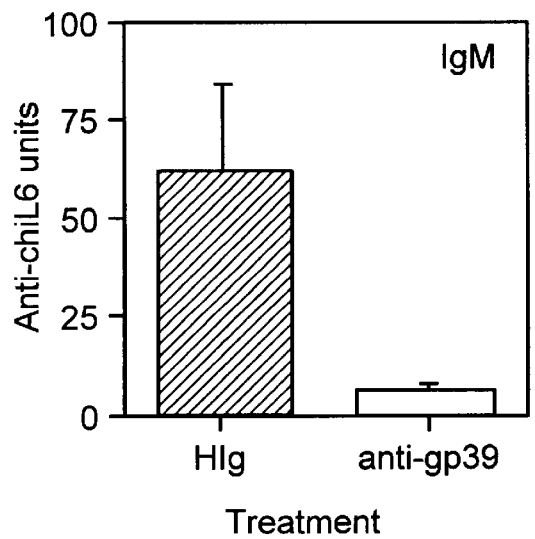
FIG. 3 is two bar graphs depicting suppression of primary anti-ChiL6 IgM antibody production (left) and secondary anti-ChiL6 IgG1 antibody production (right) by in vivo anti-gp39 treatment.
Figure 3B:
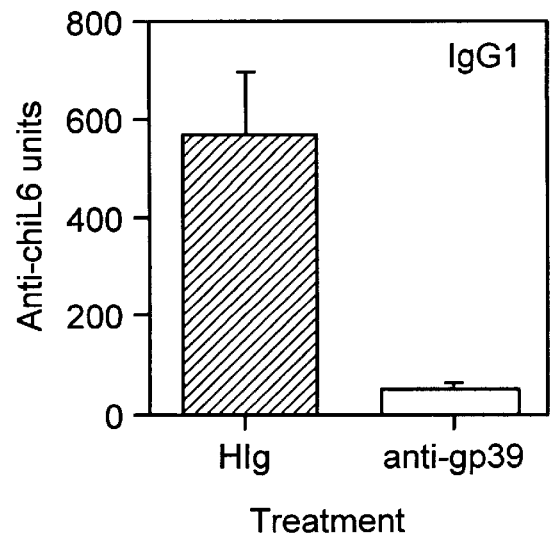

Experiments depicted in FIG. 1 demonstrate the immunosuppressive activity of anti-gp39 during a primary response to a strongly immunogenic particulate antigen, SRBC. The cellular nature of erythrocytes makes them unique in their capacity to elicit strong immune responses. Heterologous Ig molecules share this characteristic of being highly immunogenic, and therefore provide an additional model antigen system with which to examine the effects of anti-gp39 treatment on the generation of primary and secondary antibody responses. Animals were immunized with a heterologous Ig molecule, Chi-L6, a humanized mouse anti-tumor cell mAb, and treated with anti-gp39 or control HIg. After 7d, sera was collected and assayed for the production of IgM anti-Chi-L6 antibodies In addition, mice were challenged with Chi-L6 14d after initial immunization and anti-gp39 treatment, and assayed for IgG$_1$ anti-Chi-L6 antibody production on d21. FIG. 3 depicts the results of one such experiment. The primary antibody response to Chi-L6 in mice treated with anti-gp39 is inhibited by >90% when compared to HIg-treated mice. Moreover, the secondary, IgG$_1$ response to Chi-L6 is similarly inhibited. These results demonstrate that anti-gp39 treatment ablates primary and secondary antibody responses to a second type of TD antigen, heterologous Ig, as effectively as it suppresses responses to erythrocyte and soluble protein antigens.

EXAMPLE 4

Anti-gp39 Does Not Inhibit the Generation of Primary Antibody Responses to the T-Independent Type II Antigen, TNP-Ficoll.

Figure 4A:
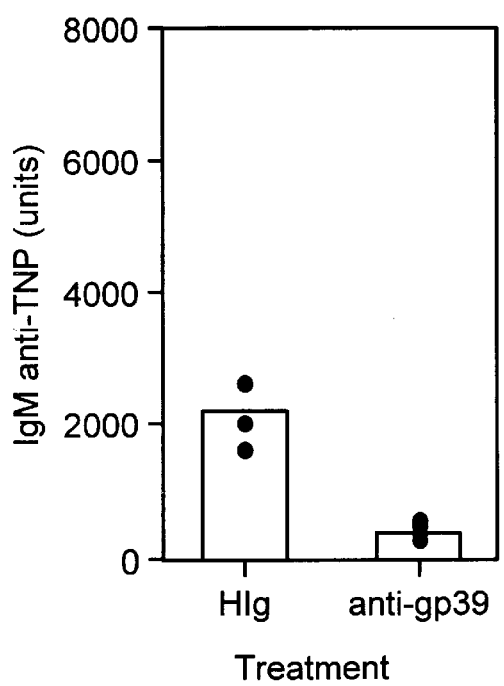
FIG. 4A is a bar graph depicting suppression of primary anti-TNP IgM antibody production by immunization with TNP-SRBC and in vivo anti-gp39 treatment.
Figure 4B:
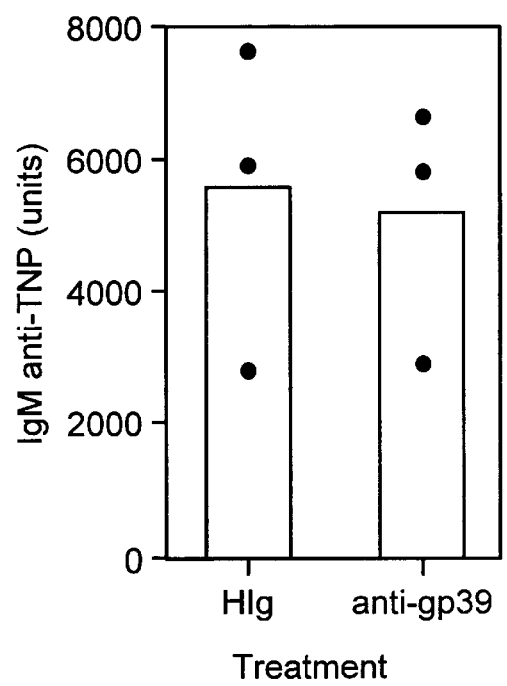
FIG. 4B is a bar graph depicting lack of suppression of primary anti-TNP IgM antibody production by immunization with TNP-Ficoll and in vivo anti-gp39 treatment.

Although the previous experiments demonstrate that anti-gp39 effectively blocks the generation of primary and secondary antibody responses to TD antigens in vivo, it is unclear whether gp39-CD40 interactions play a role in the initiation of humoral responses to TI antigens. Data presented in the accompanying paper demonstrate that immunization with the TI-type II antigen, TNP-Ficoll, results in gp39 expression by $T_h$ cells in vivo. In order to address whether gp39-CD40 interactions are necessary for the generation of antibody responses to this TI antigen, the affect of anti-gp39 treatment on mice immunized TNP-Ficoll, was assessed. Mice immunized with TNP-Ficoll or TNP-SRBC were treated with anti-gp39 or HIg and the IgM anti-TNP antibody response determined after 6 days. FIG. 4A demonstrates that animals immunized with the TD antigen TNP-SRBC elicit significant anti-TNP serum antibody responses. As predicted from the previously described experiments, anti-gp39 treatment dramatically inhibits the primary anti-TNP response generated in these mice. In contract, mice immunized with TNP-Ficoll mount a higher titered anti-TNP antibody response (FIG. 4B); however, treatment with anti-gp39 does not inhibit the antibody response to TNP-Ficoll. Results from these experiments demonstrate that, unlike responses to TD antigens, anti-gp39 does not block the generation of humoral responses to TNP-Ficoll, suggesting that responses to TI antigens may be gp39-independent.

EXAMPLE 5

Anti-gp39 Administration Does Not Functionally Delete SRBC-Specific $T_h$

Figure 5:
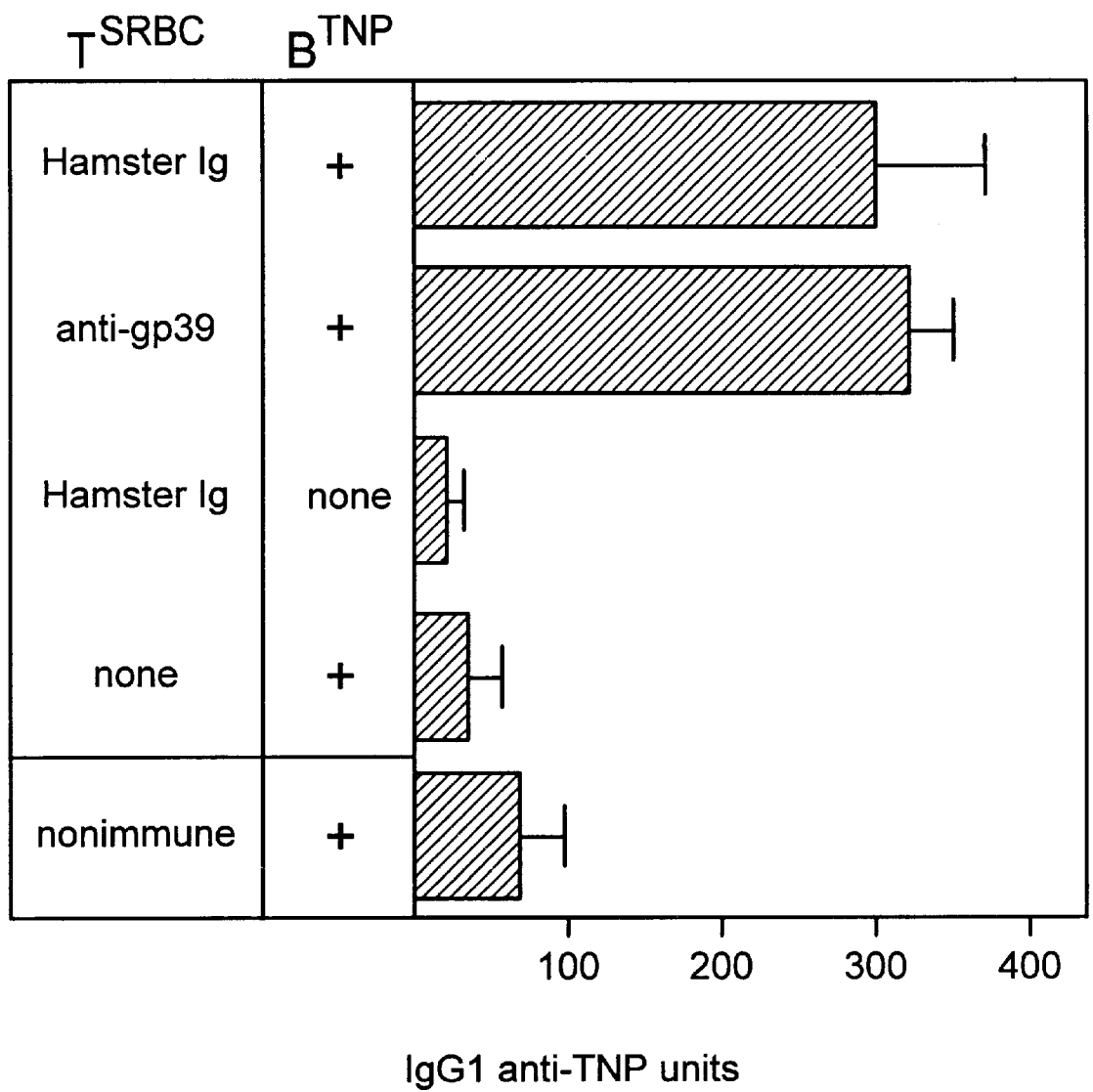
FIG. 5 is a bar graph depicting intact helper activity of T cells previously exposed to anti-gp39 treatment in vivo upon adoptive transfer to untreated mice, demonstrating that anti-gp39 administration does not functionally delete Th cells.

From the previous experiments, it is known that anti-gp39 interferes with the development of TD humoral immunity; however, the mechanism by which anti-gp39 treatment suppresses humoral responses is not clear. Immune suppression by anti-gp39 could be mediated by: 1) the negative signalling of gp39-bearing T cells causing $T_h$ anergy; 2) mAb-mediated cytotoxic deletion of anti-gp39 bearing $CD4^+$ T cells; and/or 3) the blocking of gp39 binding to CD40. A series of experiments were performed to gain insight into which of these mechanisms may be operative in the protracted immune suppression observed with anti-gp39 therapy. To explore the possibility that antigen-specific $T_h$ were deleted or anergized by anti-gp39 therapy, antigen-specific $T_h$ fuiction from gp39-treated mice was measured by adoptive transfer. Briefly, mice were immunized with SRBC (to prime SRBC-specific $T_h$) and administered anti-gp39 or HIg (250 μg/mouse on d0, d2, d4). After 7d, spleen cells from unimmunized mice or SRBC-immune spleen cells from HIg-treated or anti-gp39-treated mice were adoptively transferred into recipient mice with TNP-immune spleen cells as a source of TNP-primed B cells. Mice were simultaneously challenged with TNP-SRBC, and the $IgG_1$ anti-TNP titer ascertained on d5. SRBC-primed T helper cells are required to elicit a secondary anti-TNP response in the recipient mice as demonstrated by the fact that recipients which received spleen cells from nonimmune donors produced substantially lower IgG1 anti-TNP compared to those mice which received spleen cells from SRBC-primed animals (FIG. 5). More importantly, results of these experiments revealed that the SRBC helper activity from HIg-treated and anti-gp39-treated mice was similar, indicating that anti-gp39 treatment did not alter $T_h$ function or block the priming of $T_h$. Moreover, antigen-responsive $T_h$ were not deleted or anergized as a result of anti-gp39 treatment, as they provided helper-effector function upon transfer.

EXAMPLE 6

In Vivo Clearance of Hamster Anti-gp39.

Figure 6A:
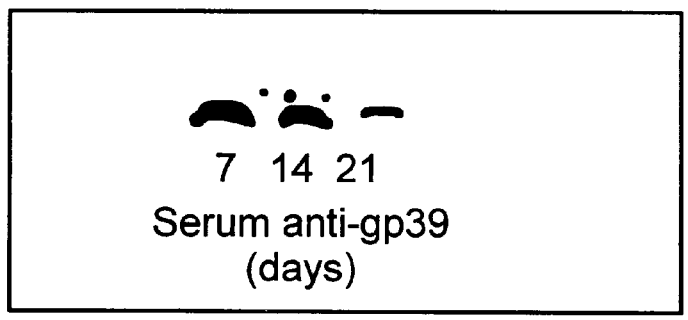
FIG. 6A is a Western blot depicting anti-gp39 antibody present in serum 7, 14 and 21 days after in vivo administration.

Previous studies have established that anti-gp39 (MR1) blocks the binding of gp39 to CD40 (15) and thus support the hypothesis that the in vivo immunosuppressive effects of anti-gp39 are due to the blocking of gp39-CD40 interactions. Assuming this hypothesis correct, the long-term immune suppression observed with anti-gp39 administration requires the persistence of anti-gp39 in the host. To determine if anti-gp39 could be detected for the period of time that immune suppression was evident, the in vivo clearance rate of anti-gp39 from serum was determined. Mice were given a regime of antibody (3×250 μg anti-gp39) over the course of 4d and assayed for the levels of serum anti-gp39 at 7d, 14d, and 21d after the initiation of antibody administration. Western blot analysis for non-reduced MR1 (160 kd) indicated that intact, serum anti-gp39 could be detected for at least 21d after the initiation of antibody treatment (FIG. 6A). The serum concentration of anti-gp39 in animals at 21d was approximately 5% (based on scanning densitometry), when compared to the signals derived from serum of animals analyzed 7d after initiation of antibody therapy.

Figure 6B:
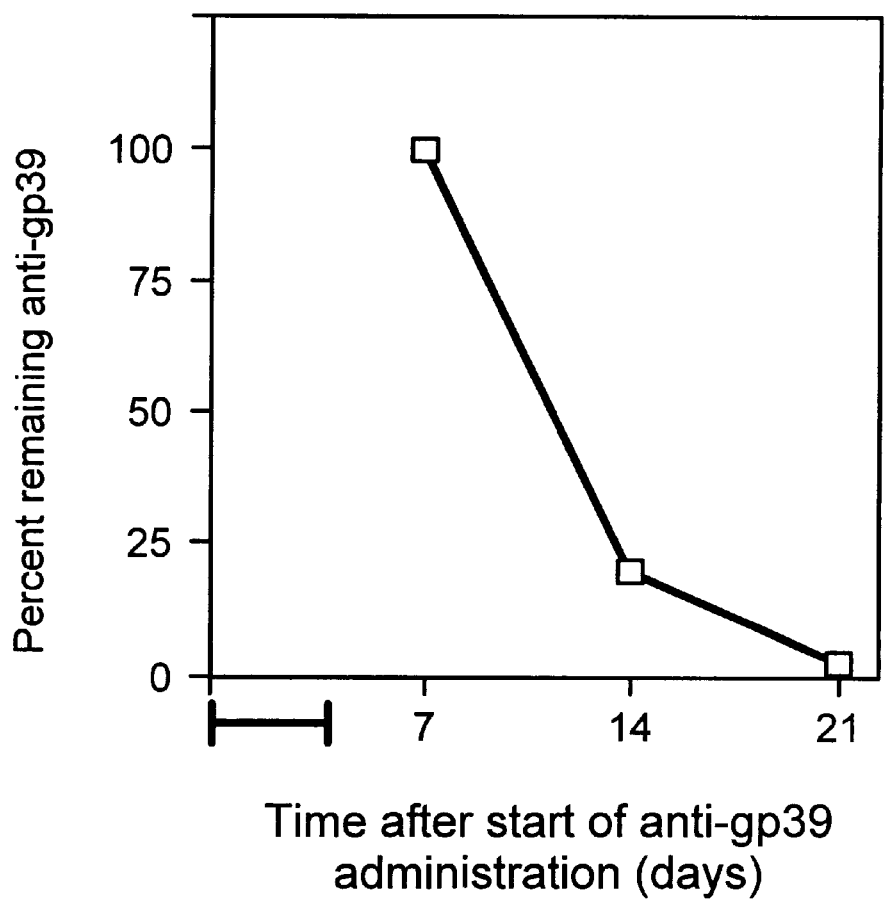
FIG. 6B is a graph depicting percent of remaining anti-gp39 activity in serum 7, 14 and 21 days after in vivo administration.

Although it was determined that intact anti-gp39 was present in serum, it was also important to ascertain that the anti-gp39 was biologically active. Therefore, sera from mice which received 3×250 μg of anti-gp39 over the course of 4d were used to stain gp39-bearing $T_h$ (FIG. 6B). The level of serum anti-gp39 3d after the last injection (7d after initiation of antibody treatment) was set at 100%. Fourteen days after the initiation of antibody therapy, approximately 10–15% of the biologically active anti-gp39 mAb was detected in the serum. Twenty-one days post-initiation of therapy, 2–3% of anti-gp39 remained in the serum. Therefore, both the determination of intact gp39 by Western blotting and of biologically active anti-gp39 revealed that approximately 5% of the anti-gp39 was present 21 d after beginning anti-gp39 therapy. These results demonstrate the half-life of anti-gp39 to be approximately 12d and offer evidence consistent with the hypothesis that prolonged suppression of humoral immune responses by anti-gp39 is due to persistent blocking of $T_h$ function.

The present study demonstrates that in vivo administration of an anti-gp39 antibody which blocks gp39-CD40 interactions in vitro, results in profound inhibition of both primary and secondary humoral immune responses to TD antigens, but not TI-type II antigens. In addition, this study demonstrates that anti-gp39 treatment does not block the priming of antigen-primed $T_h$ cells. Therefore, the gp39-CD40 ligand-receptor pair can be used as a target for the therapeutic manipulation of the humoral immune response.

To gain insight into how anti-gp39 was exerting its immunosuppressive effect on humoral immunity, the direct effects of anti-gp39 on $T_h$ function were addressed. The data indicate that SRBC-immune $T_h$ from anti-gp39-treated mice were fully capable of providing help upon adoptive transfer, suggesting that anti-gp39 treatment did not cause $T_h$ deletion or anergy in vivo. These results led to the speculation that anti-gp39 mediates its immunosuppressive effects by blocking gp39 binding to CD40 and not by the inactivation of gp39-bearing $T_h$. In support of this hypothesis in vitro studies have established that anti-gp39 blocks the binding of CD40 to gp39 (16). Furthermore, biologically active anti-gp39 could be detected in serum for the period of time that immune suppression was apparent. Although only 5% of anti-gp39 was present in serum at a time when immune suppression was evident, it is possible that the local tissue concentrations of anti-gp39 in specific sites of secondary lymphoid organs is higher and clearance rates are slower than that of serum anti-gp39.

Treatment of mice with anti-gp39 inhibited the primary immune response to SRBC and heterologous Ig >90% for prolonged periods of time. Assuming that anti-gp39 is mediating the inhibition by blocking gp39 function, these data implicate gp39-CD40 interactions as essential in the development of primary immune responses to TD antigens. Immunohistochemical analysis establish that gp39 is induced as a consequence of immunization with TD antigens and may be of functional significance. The in situ studies of gp39 expression illustrate that the initial site of gp39-CD40 interactions during primary humoral immune responses is in the peripheral aspects of the periarteriolar lymphoid sheaths (PALS) and around the terminal arterioles (TA) of the spleen. It is at these sites that conjugates between gp39-expressing $T_h$ and antigen-specific B cells were found juxtaposed, suggesting that the outer PALS is a major site of T cell-B cell interactions during primary humoral immune responses. Therefore, the PALS may be the site at which anti-gp39 interacts with gp39-expressing $T_h$ cells to ultimately inhibit T-B interaction and subsequent Ig production.

Similar to primary responses, the secondary humoral immune response of mice primed to KLH in CFA was also shown to be inhibited by the administration of anti-gp39. Consistent with the reduction of anti-SRBC PFC by anti-gp39, reductions in serum antibodies titers to antigenic challenge were also observed. The serum titers of all anti-KLH Ig isotypes measured (IgM, $IgG_1$, $IgG_{2a}$, $IgG_{2b}$, $IgG_3$, and IgE) were reduced by the treatment of mice with anti-gp39. The effect of anti-gp39 administration was apparent for at least 14d after secondary challenge with antigen, establishing a persistent immune suppression by anti-gp39. Anti-gp39-mediated immune suppression of secondary responses to KLH is not unique to KLH, since secondary immune responses to heterologous Ig and heterologous erythrocytes were also inhibited by anti-gp39 therapy. The anatomical distribution of gp39-expressing $T_h$ was identical to that observed upon primary immunization, however, the frequency of gp39-expressing Th in immune spleen was increased over that observed during primary immune responses. No gp39-expressing $T_h$ were found in the germinal centers or follicles of immune spleen. Thus, it appears that B cells are triggered to respond to activated $T_h$ cells in the PALS and TA of the spleen and later migrate to the follicles and germinal centers.

The focus of the present study was to demonstrate the potential use of anti-gp39 in the control of TD humoral immunity. Brief treatment regimes with anti-gp39 resulted in prolonged suppression, an attractive attribute of this therapeutic antibody. Of special interest may be the capacity of anti-gp39 to prevent primary and secondary humoral responses to other heterologous, therapeutic antibodies such as Chi-L6. This would permit the exposure of patients to repeated administrations of heterologous therapeutic antibodies.

The following references are refered to by number in the examples and detailed description of the invention:
1. Inaba K., M. D. Witmer, R. M. Steinman. 1984. Clustering of dendritic cells, helper T lymphocytes, and B cells during primary antibody responses in vitro. *J. Exp. Med.* 160:858.
2. Inaba K., R. M. Steinman. 1985. Protein-specific helper T-lymphocyte formation initiated by dendritic cells. *Science.* 229:475.
3. Noelle R. J., E. C. Snow. 1991. Cognate interactions of helper T cells and B cells. *Immunol. Tod.* 11:361.
4. Gordon J., M. J. Millsum, G. R. Guy, J. A. Ledbetter. 1987. Synergistic interaction between interleukin 4 and anti-Bp50 (CDw40) revealed in a novel B cell restimulation assay. *Eur. J. Immunol.* 17:1535.
5. Clark E. A., J. A. Ledbetter. 1986. Activation of human B cells mediated through two distinct cell surface differentiation antigens, Bp35 and Bp 50. *Proc. Natl. Acad. Sci. USA.* 83:4494.
6. Stamenkovic I., E. A. Clark, B. Seed. 1989. A B-lymphocyte activation molecule related to the nerve growth factor receptor and induced by cytokines in carcinomas. *EMBO.* 8:1403.
7. Hollenbaugh D., L. Grosmaire, C. D. Kullas, N. J. Chalupny, R. J. Noelle, I. Stamenkovic, J. A. Ledbetter, A. Aruffo. 1992. The human T cell antigen p39, a member of the TNF gene family, is aligand for the CD40 receptor: Expression of a soluble form of gp39 with B cell co-stimulatory activity. *EMBO.* 11:4313.
8. Armitage R. J., W. C. Fanslow, L. Strockbine, T. A. Sato, K. N. Clifford, B. M. Macduff, D. M. Anderson, S. D. Gimpel, T. Davis-Smith, C. R. Maliszewski, E. A. Clark, C. A. Smith, K. H. Grabstein, D. Cosman, M. K. Spriggs. 1992. Molecular and biological characterization of a murine ligand for CD40. *Nature.* 357:80.
9. Valle A., C. E. Zuber, T. Defrance, O. Djossou, R. M. De, J. Banchereau. 1989. Activation of human B lymphocytes through CD40 and interleukin 4. *Eur. J. Immunol.* 19:1463.
10. Gordon J., M. J. Millsum, R. L. Flores, S. Gillis. 1989. Regulation of resting and cycling human B lymphocytes via surface the accessory molecules interleukin-4, CD23 and CD40. *Immunology.* 68:526.
11. Jabara H. H., S. M. Fu, R. S. Geha, D. Vercelli. 1990. CD40 and IgE: synergism between anti-CD40 monoclonal antibody and interleukin 4 in the induction of IgE synthesis by highly purified human B cells. *J. Exp. Med.* 172:1861.
12. Banchereau J., F. Rousset. 1991. Growing human B lymphocytes in the CD40 system. *Nature.* 353:678.
13. Armitage R. J., T. A. Sato, B. M. Macduff, K. N. Clifford, A. R. Alpert, C. A. Smith, W. C. Fanslow. 1992. Identification of a source of biologically active CD40 ligand. *Eur. J. Immunol.* 22:2071.
14. Lane P., A. Traunecker, S. Hubele, S. Inui, A. Lanzavecchia, D. Gray. 1992. Activated human T cells express a ligand for the human B cell-associated antigen CD40 which participates in T cell-dependent activation of B lymphocytes. *Eur. J. Immunol.* 22:2573.
15. Noelle R. J., J. A. Ledbetter, A. Aruffo. 1992. CD40 and its ligand, an essential ligand-receptor pair for thymus-dependent B cell activation. *Immunol. Tod.* 13:431.
16. Noelle R. J., M. Roy, D. M. Shepherd, I. Stamenkovic, J. A. Ledbetter, A. Aruffo. 1992. A novel ligand on activated T helper cells binds CD40 and transduces the signal for the cognate activation of B cells. *Proc. Natl. Acad. Sci. USA.* 89:6550.
17. Allen R. C., R. J. Armitage, M. E. Conley, H. Rosenblatt, N. A. Jenkins, N. G. Copeland, M. A. Bedell, S. Edelhoff, J. Disteche, D. K. Simoneaux, W. C. Fanslow, J. Belmont, M. K. Spriggs. 1993. CD40 ligand gene defects responsible for X- linked hyper- IgM Syndrome. *Science.* 259:990.
18. Aruffo A., M. Farrington, D. Hollenbaugh, Li X., A. Milatovich, S. Nonoyama, J. Bajorath, L. S. Grosmaire, R. Stenkamp, M. Neubauer, R. L. Roberts, R. J. Noelle, Ledbetter, U. J. A. Francke, H. D. Ochs. 1993. The CD40 ligand, gp39, is defective in activated T cells from patients with X- linked hyper- IgM syndrome. *Cell.* 72:291.
19. DiSanto J. P., J. Y. Bonnefoy, J. F. Gauchat, A. Fischer, G. de Saint Basile. 1993. CD40 ligand mutations in X-linked immunodefiency with hyper- IgM. *Nature.* 361:541.

20. Korthauer U., D. Graf, H. W. Mages, F. Brieres, M. Padayachee, S. Malcolm, A. G. Ugazio, L. D. Notarangelo, R. L. Levinsky, A. Kroczek. 1993. Defective Expression of T- cell CD40 ligand causes X- linked immunodeficiency with hyper- IgM. *Nature.* 361:539.

21. Kurt-Jones E., S. Hamberg, J. Ohara, W. E. Paul, A. K. Abbas. 1987. Heterogeneity of helper/inducer T lymphocytes. I. Lymphokine production. *J. Exp. Med.* 166:1774.

22. Springer T. A., A. Bhattacharya, J. T. Cardoza, F. Sanchez-Madrid. 1982. Monoclonal antibodies specific for rat IgG1, IgG2a, and IgG2b subclasses, and kappa chain monotypic and allotypic determinants: reagents for use with rat monoclonal antibodies. *Hybrid.* 1:25.

23. Hellstrom I. 1986. Monoclonal mouse antibodies raised against human lung carcinoma. *Can. Res.* 46:3917.

24. Wilde D. B., P. Marrack, J. Kappler, D. P. Dialynas, F. W. Fitch. 1983. Evidence implicating L3T4 in class II MHC antigen reactivity; monoclonal antibody GK1.5 (anti-L3T4a) blocks class II MHC antigen-specific proliferation, release of lymphokines, and binding by cloned murine helper T lymphocyte lines. *J. Immunol.* 131:2178.

25. Snow E. C., R. J. Noelle. 1987. Thymus-dependent antigenic stimulation of hapten-specific B lymphocytes. *Immunol. Rev.* 99:173.

26. Jerne N. K. C. Henry, A. A. Nordin, H. Fuji, A. M. Koros, and I. Lefkovits. 1974. Plaque forming cells: Methodology and theory. *Transplant Rev.* 18:130.

27. Ochs H. D., R. J. Wedgewood. 1989. Disorders of the B cell system. In Immunologic disorders in infants and children, Third ed., E. R. Sreihm, ed. (Philadelphia: W. B. Saunders), pp. 226.

28. Notarangelo L. D., M. Duse, A. G. Ugazio. 1992. Immunodeficiency with hyper-IgM (HIM). *Immunodef. Rev.* 3:101.

29. Shizuru J. A., S. A. Alters, C. G. Fathman. 1992. Anti-CD4 monoclonal antibodies in therapy: Creation of nonclassical tolerance in the adult. *Immunol. Rev.* 129:103.

30. Linsley P. S., P. M. Wallace, J. Johnson, M. G. Gibson, J. L. Greene, J. A. Ledbetter, C. Singh, M. A. Tepper. 1992. Immunosuppression in vivo by a soluble form of the CTLA-4 T cell activation molecule. *Science.* 257:792.

31. Lenschow D. J., Y. Zeng, J. R. Thistlethwaite, A. Montag, W. Brady, M. G. Gibson, P. S. Linsley, J. A. Bluestone. 1992. Long-term survival of xenogeneic pancreatic islet grafts induced by CTLA41g. *Science.* 257:789.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for inducing prolonged inhibition of a humoral immune response to a thymus dependent (TD) antigen in vivo, comprising administering a therapeutic agent which is a thymus dependent (TD) antigen to a subject in need of such treatment, wherein said humoral immune response is a primary immune response or a secondary immune response, and further administering to said subject prior, subsequent, or concurrent to the administration of said therapeutic agent an amount of a gp39 (CD40 ligand) antagonist selected from the group consisting of anti-gp39 antibodies, fragments of said antibodies which specifically bind gp39, soluble CD40 and soluble CD40 fusion proteins which is sufficient to provide for prolonged inhibition of a humoral immune response to said administered therapeutic agent, wherein prolong inhibition means that suppression of antibody production against said therapeutic agent is maintained after administration of said gp39 antagonist has been discontinue.

2. The method of claim 1 wherein said therapeutic agent and said gp39 antagonist are administered concurrently.

3. The method of claim 1 wherein said therapeutic agent is administered after administration of said gp39 antagonist.

4. The method of claim 1 wherein said therapeutic agent is administered prior to administration of said gp39 antagonist.

5. The method of claim 1 wherein said therapeutic agent is selected from the group consisting of drugs, proteins, antibodies, and haptens.

6. The method of claim 1 wherein the therapeutic agent is an antibody.

7. The method of claim 1 wherein the therapeutic agent is a protein.

8. The method of claim 1 wherein the gp39 antagonist is an anti-gp39 antibody or fragment of said anti-gp39 antibody that specifically binds gp39.

9. The method of claim 8 wherein said anti-gp39 antibody is an anti-human gp39 antibody.

10. The method of claim 9 wherein said antibody is a monoclonal antibody containing constant and variable regions obtained from antibodies of different species.

11. The method of claim 9 wherein said antibody is a humanized antibody.

12. The method of claim 9 wherein said antibody is a bispecific antibody.

13. The method of claim 9 wherein said antibody fragment is selected from the group consisting of F(ab')$_2$ Fab, V$_H$ and F$_v$.

14. The method of claim 9 wherein said antibody is a human antibody or fragment of said anti-gp39 antibody that specifically binds gp39.

15. The method of claim 1 which further includes administration of anti-IL-4 antibody.

16. The method of claim 1 which results in the suppression of a primary humoral immune response.

17. The method of claim 1 which results in the suppression of a secondary humoral immune response.

* * * * *

UNITED STATES PATENT AND TRADEMARK OFFICE
CERTIFICATE OF CORRECTION

PATENT NO. : 5,942,229
DATED : August 24, 1999
INVENTOR(S) : Noelle et al

It is certified that error appears in the above-identified patent and that said Letters Patent is hereby corrected as shown below:

COL. 20     line 16, delete "prolong" and replace with --prolonged--;

COL. 20     line 19, delete "discontinue" and replace with --discontinued--;

COL. 20     line 47, delete "F(ab')$_2$" and replace with --F(ab')$_2$,--.

Signed and Sealed this

Twentieth Day of March, 2001

Attest:

NICHOLAS P. GODICI

Attesting Officer     Acting Director of the United States Patent and Trademark Office